United States Patent [19]
Saito et al.

[11] Patent Number: 5,611,779
[45] Date of Patent: Mar. 18, 1997

[54] ELECTROCHEMICAL FLUID DELIVERY DEVICE

[75] Inventors: Satoshi Saito; Yuko Fujita; Akio Tokunaga, all of Kyoto, Japan

[73] Assignee: Japan Storage Battery Co., Ltd., Kyoto, Japan

[21] Appl. No.: 388,850

[22] Filed: Feb. 15, 1995

[30]     Foreign Application Priority Data

Feb. 17, 1994 [JP] Japan .................................. 6-044961

[51] Int. Cl.$^6$ .............................................. A61M 5/20
[52] U.S. Cl. ...................................... 604/156; 604/890.1
[58] Field of Search ................................ 606/156, 124, 606/125, 167, 169, 159, 236, 134, 136, 157; 417/379

[56]              References Cited

U.S. PATENT DOCUMENTS

| | | | |
|---|---|---|---|
| 2,626,604 | 1/1953 | Nadeau | 604/156 |
| 4,140,117 | 2/1979 | Buckles et al. | 128/213 R |
| 4,495,078 | 1/1985 | Bell et al. | 252/62.2 |
| 4,687,423 | 8/1987 | Maget et al. | 417/379 |
| 4,813,938 | 3/1989 | Raulerson | 604/156 |
| 4,886,514 | 12/1989 | Maget | 604/891.1 |
| 4,902,278 | 2/1990 | Maget et al. | 604/132 |
| 5,300,030 | 4/1994 | Crossman | 604/156 |
| 5,545,139 | 8/1996 | Kriesel | 604/890.1 |
| 5,558,664 | 9/1996 | Sarzaud | 604/890.1 |

FOREIGN PATENT DOCUMENTS

| | | | |
|---|---|---|---|
| 0385916 | 9/1990 | European Pat. Off. | A61M 5/155 |
| 0563501 | 10/1993 | European Pat. Off. | A61M 5/155 |
| 58-48209 | 10/1983 | Japan | B01J 7/02 |
| 2302264 | 12/1990 | Japan | A61M 5/142 |
| 9325841 | 12/1993 | WIPO | F16N 11/10 |
| 9426329 | 11/1994 | WIPO | A61M 5/155 |

*Primary Examiner*—Michael A. Brown
*Attorney, Agent, or Firm*—Sughrue, Mion, Zinn, Macpeak & Seas

[57]                ABSTRACT

An electrochemical fluid delivery device of the present invention includes a case, pressure generating part and fluid reservoir part. The case has a cover capable of being opened and closed. When the cover is closed after the fluid reservoir part is accommodated in the case, the inside of the case can be maintained in an airtight condition. The pressure generating part includes a power supply part and electrochemical cell part. When a direct current flows in the electrochemical cell part, gas is generated and accumulates in the airtight case. By the pressure of gas, the fluid reservoir part is pressurized so that the fluid can be delivered. The amount of gas generated at constant pressure by the electrochemical cell part is determined by a quantity of electricity (current× time). Since the amount of fluid to be delivered is proportional to the amount of generated gas, the amount of fluid to be delivered in a unit time can be determined by the intensity of a current. A total amount of delivered fluid can be determined by the quantity of electricity.

19 Claims, 4 Drawing Sheets

ELECTROCHEMICAL FLUID DELIVERY DEVICE

BACKGROUND OF THE INVENTION

1. Field of the Invention

The present invention relates to a fluid delivery device for accurately delivering fluid little by little.

2. Description of the Conventional Art

Recently, in order to inject liquid medicine into human's body with accuracy, various types of infusion pumps are used.

The conventional infusion pumps are classified into 4 types, which are a syringe pump, peristaltic (rotor type) pump, finger pump and bellows pump. Except for the bellows pump, each of the above infusion pumps is provided with a stepping motor, rotary solenoid motor or DC motor so that liquid medicine can be delivered by a drive force generated by the motor. Accordingly, since a complicated control mechanism is adopted to control an infuse volume of the liquid medicine, the weights and dimensions of these pumps are usually large and further their cost is expensive. Therefore, it is common that these pumps are used beside the bed in a hospital, and they are not suitable for portable or disposable use. In the bellows pump, vaporization pressure of freon gas is utilized, and liquid medicine is delivered by the action of vaporization pressure. However, it is difficult to control the vaporization pressure of freon gas. Especially when a very small amount of liquid medicine is injected over a long period of time, the accuracy of the injection is difficult to maintain.

One of the present inventors made an application for a patent of the apparatus having a pumping function where the rate of gas flow is controlled with an electrochemical cell in which gas is generated when a direct current is made to flow (Unexamined Japanese Patent Publication No. Sho. 58-48209). Recently, an electrochemically driven drug dispenser has been proposed, in which the aforementioned principle is adopted. In this system, liquid medicine is delivered by the action of gas generated in proportion to a quantity of electricity when a direct current is made to flow in the electrochemical cell part. According to the invention proposed by H. J. R. Maget disclosed in U.S. Pat. Nos. 4,687,423, 4,886,514 and 4,902,278, the electrochemical cell is composed of a polymer electrolyte membrane and a pair of electrodes attached onto both sides of the electrolyte membrane. In this cell, when a current is allowed to flow between both electrodes so that an electrochemical active mass is supplied to the first electrode, the electrochemical active mass is ionized there, and the generated ions move through the electrolyte membrane and arrive at the second electrode. At the second electrode, ions are converted into a pressurized gas, which is used as a drive source for pushing the diaphragm. When hydrogen is used as the electrochemical active mass, hydrogen functions as the pressurized gas. On the other hand, when oxygen and air are used as the electrochemical active mass, oxygen functions as the pressurized gas.

However, in the drug dispenser disclosed in U.S. Pat. No. 4,687,423, gas is pressurized by the electrochemical cell, and is released through a pump valve when its pressure is increased to a predetermined value. By the action of this gas pressure, a flexible diaphragm is subjected to pulsation so that the liquid medicine in a pump chamber is delivered. When this drug dispenser is operated, a current is made to flow in a predetermined direction, however, it is necessary to accurately adjust a relation between the pressure required for expanding and contracting the flexible diaphragm including a part of the wall of the pump chamber and the pressure required for operating a pump valve of the pressure release mechanism. Further, the electrochemical cell, pump chamber and pressure release mechanism are integrated into one unit. Therefore, when different types of medicines are used, the pump chamber must be washed each time. Further, the structure of the apparatus is considerably complicated. As a result, the cost of the apparatus is increased. Therefore, it is impossible to put the pump into disposable use.

In the drug dispenser described in U.S. Pat. No. 4,886,514, the electrochemical pump and liquid medicine container are integrated into one unit in which a flexible diaphragm, bellows or sliding wall provided for separating the electrochemical pump from the liquid medicine container is deformed or moved so that the medicine in the medicine container can be delivered. In this drug dispenser, since the electrochemical pump and medicine container are integrated into one unit, they can not be separated from each other. Accordingly, it is difficult to put this apparatus in disposable use. Further, this apparatus also has some disadvantages such that the medicine container must be washed each time when different types of liquid medicines are used.

In the fluid delivery pump described in U.S. Pat. No. 4,902,278, a prime mover portion in which the power supply part and electrochemical cell part are integrated into one unit can be separated from the fluid reservoir part, and a flexible membrane of the fluid reservoir part is pushed by the gas generated from the prime mover part so that the fluid can be delivered. However, the structure of the fluid reservoir part of this apparatus is complicated. Therefore, the fluid reservoir part is not suitable for disposable use. Further, it is complicated to put liquid medicine into the fluid reservoir part.

For a remodeled pump of this electrochemical liquid transporting pump, there is provided a method in which electrolysis of water is used (Unexamined Japanese Patent Publication No. Hei. 2-302264). According to this method, an electrochemical cell is used in which a cathode is integrally joined on one side of an ion exchange membrane and an anode is integrally joined on the other side of the ion exchange membrane. Alternatively, an electrochemical cell is used in which a cathode and anode are integrally joined on one side of an ion exchange membrane under the condition that the cathode and anode are separated from each other so that they can be insulated. Water is contained in the above electrochemical cell, and a direct current is made to flow in both electrodes so that hydrogen and oxygen are generated by the electrolysis of water. Generated hydrogen or oxygen, or alternatively mixture gas of hydrogen and oxygen is used for the pressure source of the liquid infusion pump.

SUMMARY OF THE INVENTION

The present invention has been developed to solve the above problems of the electrochemically driven drug dispenser. An object of the present invention is to provide a simple, small, compact, portable and inexpensive electrochemical fluid delivery device easily operated in practical use where only the fluid reservoir part of the device is disposable.

The electrochemical fluid delivery device of the present invention includes a case, a pressure generating part and a fluid reservoir part. The case is provided with a cover capable of being opened and closed. When the cover is closed after the fluid reservoir part has been accommodated in the case, the inside of the case can be maintained in an airtight condition.

The pressure generating part includes a power supply part and an electrochemical cell part. When a direct current flows in the electrochemical cell part, gas is generated. This generated gas being accumulated in the airtight case pressurizes the fluid reservoir part is pressurized, so that the fluid can be delivered. The case and the pressure generating part may be either integrally or detachably provided. The case can be detached from the fluid reservoir part. The fluid reservoir part is provided with a fluid delivery port to which a check valve is attached for preventing a backward flow.

BRIEF DESCRIPTION OF THE DRAWINGS

In the accompanying drawings.

DETAILED DESCRIPTION OF THE PREFERRED EMBODIMENTS

The detailed description of the preferred embodiments of the present invention will be described referring to the accompanying drawings as follows.

An electrochemical fluid delivery device of the present invention includes a case, a pressure generating part and a fluid reservoir part. The pressure generating part includes an electrochemical cell part and power supply part. When a direct current flows in the electrochemical cell part, gas is generated. By the action of this generated gas, the fluid reservoir part is directly pushed, so that the fluid stored in the fluid reservoir part is pushed out. The amount of gas generated by the electrochemical cell part at constant pressure is determined by a quantity of electricity (current × time). Since the amount of fluid to be delivered is proportional to the amount of generated gas, the amount of fluid to be delivered in a unit time can be determined by the intensity of a current. A total amount of delivered fluid can be determined by the quantity of electricity. As described above, in the electrochemical fluid delivery device of the present invention, it is possible to accurately determine the amount of delivered fluid by a very simple method over a long period of time.

Figure 1:
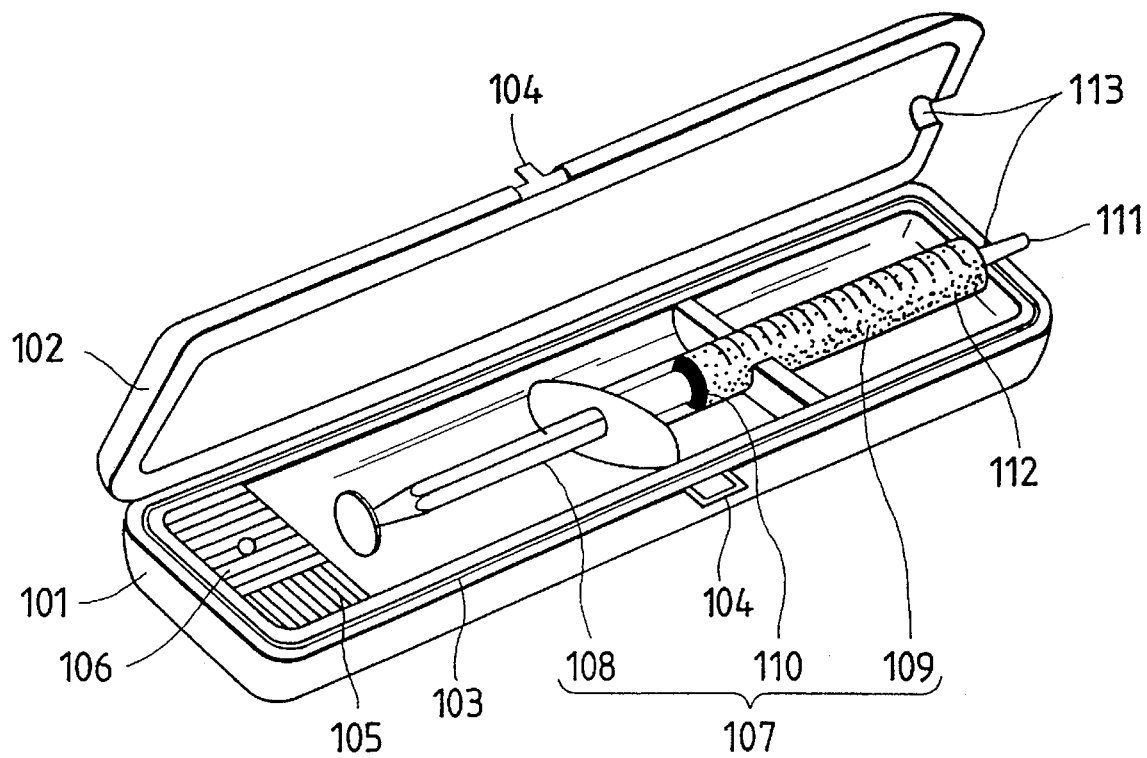
FIG. 1 is a schematic illustration of the electrochemical fluid delivery device of the present invention in which a syringe used as a fluid reservoir part is accommodated in the airtight case.

With reference to FIG. 1, the structure and operational principle of the electrochemical fluid delivery device of the present invention will be explained as follows.

FIG. 1 is a schematic illustration of the electrochemical fluid delivery device in which a syringe is used for the fluid reservoir part. In FIG. 1, numeral 101 designates a case. A cover 102, O-ring 103 and metal fitting 104 are attached to the case 101. The cover 102 is capable of being opened and closed with respect to the case 101. When the cover 102 is closed and fastened to the case 101 by the metal fitting 104, the inside of the case 101 is airtightly closed. Namely, the O-ring 103 and metal fitting 104 are used to seal the inside of the case 101 to be in airtight condition. A power supply part 105 and electrochemical cell part 106 are provided in the case 101. Numeral 107 designates a syringe to be used as the fluid reservoir part. The syringe includes a suction member 108 and an outer tube 109. A piston 110 is attached to a fore end of the suction member 108 so that the suction member 108 can be moved inside the outer tube 109 being closely contacted with the inside of the outer tube 109. Numeral 111 designates a fluid delivery port, numeral 112 designates a liquid medicine to be delivered, and numeral 113 designates a hole through which the fluid delivery port 111 is protruded from the case 101.

When this electrochemical fluid delivery device is used, first, the liquid medicine 112 is charged into the outer tube 109 of the syringe 107. Then the syringe 107 is put into the case 101, the cover 102 is closed and the metal fitting 104 is fastened so that the inside of the case 101 is maintained to be airtight. At this time, the fluid delivery port 111 provided at a fore end of the outer tube of the syringe is inserted to connect with the hole 113 or alternatively connected with the hole 113 in such a manner that the fluid delivery port 111 is located outside the case 101 so that this portion can be maintained in an airtight condition.

Next, when a direct current is made to flow in the electrochemical cell part 105, gas is generated. When the supply of electric power is continued so that the generated gas of the electrochemical cell part 105 is accumulated in the case 101, the pressure in the case 101 is rapidly increased to impress upon the suction member 108 of the syringe 107. When the pressure in the case 101 is increased higher than the frictional force between the outer tube 109 and the piston 110 of the suction member 108 of the syringe 107, the suction member 108 is moved being pushed into the outer tube 109. As a result, the liquid medicine 112 is delivered from the fluid deliver port 111 of the syringe 107 located outside the case 101.

The amount of gas generated by the electrochemical cell part is determined by a quantity of electricity (current × time). Therefore, when a constant current is made to flow, the amount of liquid medicine delivered in a unit time is maintained constant. Accordingly, when the intensity of a current and the time in which the current flows are determined, an arbitrary amount of liquid medicine can be provided.

When the fluid reservoir part is constructed in such a manner that the suction member of the syringe is removed and only the piston is provided, the same operation as that described above can be carried out. Alternatively, it is possible to use a bladder having a fluid delivery port instead of using a syringe for the fluid reservoir part.

Next, with reference to FIGS. 2A to 2F, a method by which the liquid medicine is charged into the outer tube of the syringe will be explained when the fluid reservoir part includes only the outer tube and piston. In the items FIGS. 2A to 2F, same parts are identified by the same reference numerals of 201 to 212. Numeral 201 designates an outer tube of the syringe that is the fluid reservoir part, numeral 202 designates a first piston capable of moving in the outer tube 201 being closely contacted with the inner wall, and numeral 203 designates a fluid delivery port of the outer tube of the syringe. Numeral 204 designates a suction member, which includes a tube-shaped piston rod 205 and a second piston 206 capable of moving and being closely contacted with the inner wall of the outer tube of the syringe. There is provided a small hole 207 in the second piston 206. The suction member 204 is provided with a communicating hole 209 that communicates the small hole 207 of the second piston 206 provided at a fore end with a rear end portion 208 of the suction member 204. The rear end portion 208 of the suction member 204 is open at all times. Numeral 210 designates a needle, numeral 211 designates a liquid medicine container, numeral 212 designates a liquid medicine, and numeral 213 designates a finger tip.

Figure 2A:
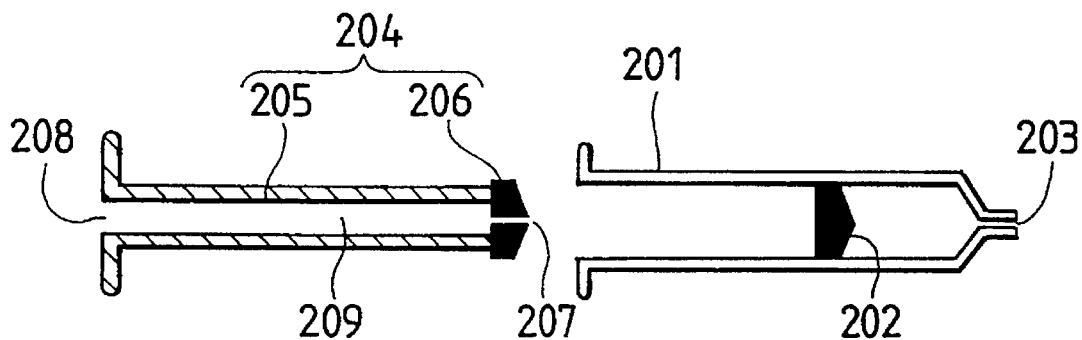
FIGS. 2A to 2F are schematic illustrations showing a method of charging a fluid into the outer tube of the syringe in the electrochemical fluid delivery device of the present invention to be explained in Example 2.

A predetermined amount of liquid medicine 212 is charged into the outer tube 201 of the syringe in accordance with the following procedure. First, as illustrated in FIG. 2A, the outer tube 201 of the syringe provided with the first piston 202 is prepared, and the suction member 204 is also prepared which includes the second piston 206 attached to an end of the tube-shaped piston rod 205.

Figure 2B:
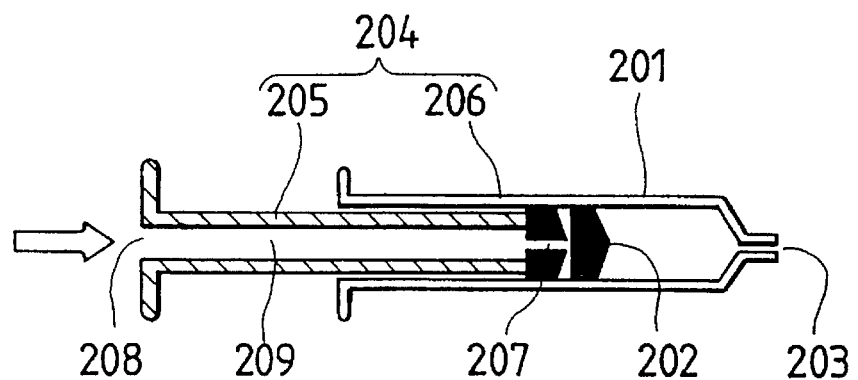
Figure 2C:
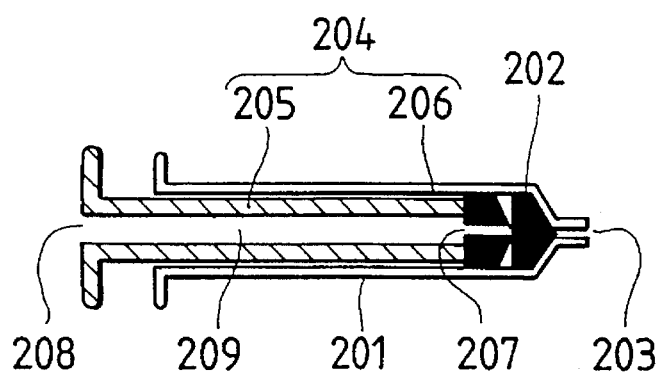

Next, as illustrated in FIG. 2B, under the condition that the rear end 208 of the suction member 204 is open, the suction member 204 is pushed into the outer tube 201 in the arrowed direction until the second piston 206 comes into contact with the first piston 202. Further, as illustrated in FIG. 2C, the suction member 204 is pushed into the outer tube 201 until the first piston 202 reaches an end of the outer tube 201. Under this condition, air in the outer tube 201 of the syringe is completely discharged from the inside of the outer tube 201 of the syringe.

Figure 2D:
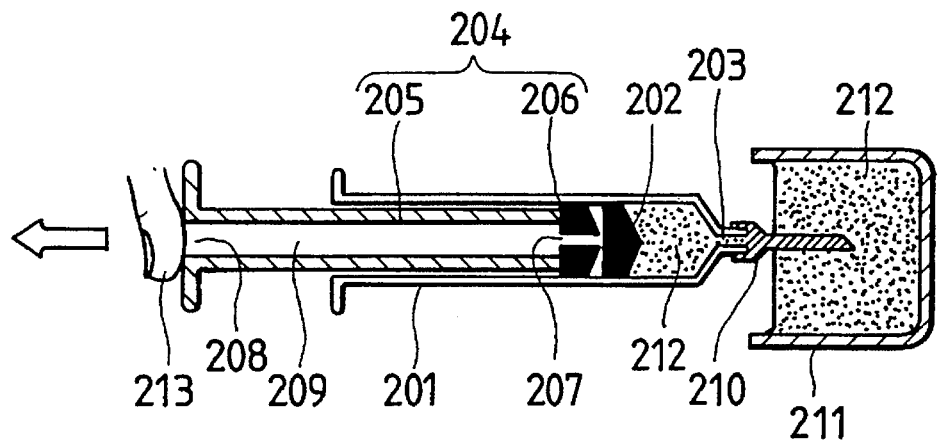
Figure 2E:
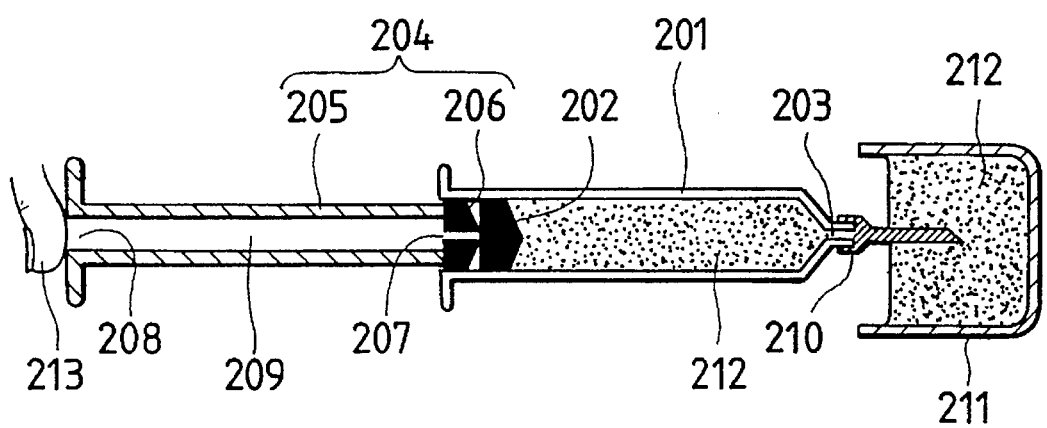
Figure 2F:
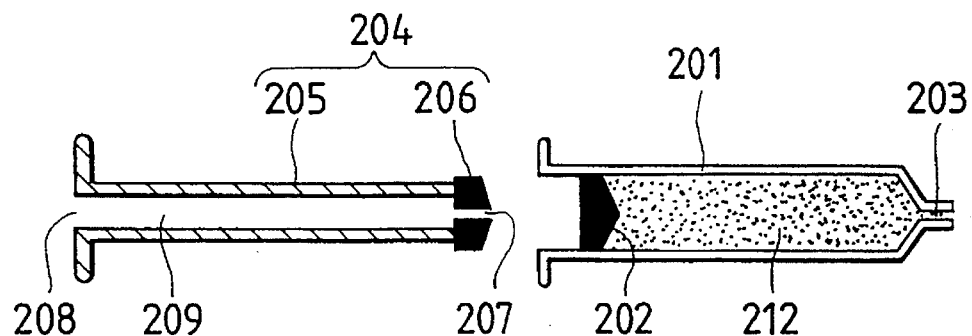

Next, as illustrated in FIG. 2D, a needle 210 is attached to the fluid delivery port 203 of the outer tube 201 of the syringe. Then the needle 210 is immersed in the liquid medicine 212 in the liquid medicine container 211. Under the condition that a rear end portion 208 of the suction member 204 is closed by the finger tip 213, the suction member 204 is moved in the arrowed direction so that the suction member 204 is pulled out from the outer tube 201. Then a space between the first and second pistons 202 and 206 is put in a decompressed condition. Accordingly, when the suction member 204 is pulled out, the first piston 202 is moved in the same direction as that of the second piston 206. As a result, the outer tube 20i of the syringe is filled with the liquid medicine 211. Next, as illustrated in FIG. 2E, the suction member 204 is pulled out from the outer tube 201 of the syringe to an arbitrary position so as to charge a predetermined amount of the liquid medicine 211 into the outer tube 201. After that, as illustrated in FIG. 2F, under the condition that the rear end portion 208 of the suction member 204 is open, the suction member 204 is further pulled out from the outer tube 201 of the syringe. Then, the suction member 204 can be removed from the outer tube 201 while the first piston 202 stays in the outer tube 201.

Usually, the liquid medicine is delivered by this electrochemical fluid delivery device. However, it should be noted that the present invention is not limited to the specific electrochemical fluid delivery device by which the liquid medicine is delivered. Of course, the present invention can be applied to an electrochemical fluid delivery device by which all types of fluid such as liquid and gas can be delivered.

EXAMPLE 1

One example of the electrochemical fluid delivery device, the fluid reservoir part of which includes a disposable syringe, will be explained, in which the fluid reservoir part is directly pushed by the gas generated in the electrochemical cell part.

A schematic illustration of the electrochemical fluid delivery device in which a syringe is used for the fluid reservoir part is the same as in FIG. 1. In FIG. 1, numeral 101 designates a case, numeral 102 designates a cover, numeral 103 designates an O-ring, and numeral 104 designates a metal fitting for fastening the case 101 with the cover 102. The cover 102 is capable of being opened and closed with respect to the case 101. When the cover 102 is closed, the inside of the case can be maintained in an air tight condition. A power supply part 105 and electrochemical cell part 106 are provided in the case 101. A water electrolysis cell is applied to the electrochemical cell part 106. The water electrolysis cell is used as the electrochemical cell part 106, where a solid polymer protonic conductor having a diameter of 12 mm, which functions as a solid electrolyte, and porous platinum electrodes having a diameter of 8 mm are provided and joined onto both sides of the solid polymer protonic conductor by means of electroless plating. One electrode is used as an anode, and the other electrode is used as a cathode. Both the anode and cathode are contacted with water. A disposable type plastic syringe 107 available in the market, the content of which is 5 ml, is used for the fluid reservoir part. The syringe includes the suction member 108 and the outer tube 109. A piston 110 is attached to a fore end of the suction member 108 so that the suction member 108 can be moved inside the outer tube 109 being closely contacted with the inside of the outer tube 109. Numeral 111 designates a fluid delivery port, numeral 112 designates a liquid medicine to be delivered, and numeral 113 designates a hole through which the fluid delivery port 111 is protruded from the case 101.

When this electrochemical fluid delivery device is used, a predetermined fluid 112 such as a liquid medicine to be delivered is charged into the outer tube 109 of the syringe 107, and the syringe 107 is arranged into the case 101. Then the cover 102 is closed with respect to the case 101, and the metal fitting 104 is fastened, so that the syringe 107 is held in the case 101 under an airtight condition while only the fluid delivery port 111 of the outer tube 109 of the syringe is protruded from the case 101.

When a direct current of 60 mA is sent from the power supply part 105 to the electrochemical cell part 106, electrolytic reactions of water occur in the electrochemical cell part 106. When the supply of electric power is maintained so that oxygen generated by the anode is accumulated in the case 101, the pressure of oxygen in the case 101 is increased. Then, when the pressure in the case 101 become higher than the frictional force between the outer tube 109 and the piston 110 of the suction member 108 of the syringe 107, the suction member 108 is pushed into the outer tube 109, whereby the liquid medicine of 6 ml per hour is delivered from the fluid deliver port 111 of the syringe 107 protruded from the case 101.

If the electrochemical cell part 105 is arranged in such a manner that hydrogen generated by the cathode accumulates in the case 101, it is sufficient that a current of 30 mA is fed. On the other hand, when the electrochemical cell part 105 is arranged in such a manner that both oxygen and hydrogen accumulate in the case 101, it is sufficient that a current of 20 mA is fed. In any cases, the amount of oxygen or hydrogen generated in the electrolysis of water is determined by a quantity of electricity (current × time). Therefore, when a constant current is made to flow, the amount of liquid medicine delivered in a unit time is maintained constant. Accordingly, when the intensity of a current is determined, an arbitrary amount of liquid medicine can be provided.

EXAMPLE 2

Other example of the electrochemical fluid delivery device of the present invention, the fluid reservoir part of which includes only an outer tube and piston of the syringe, will be explained below.

Figure 3:
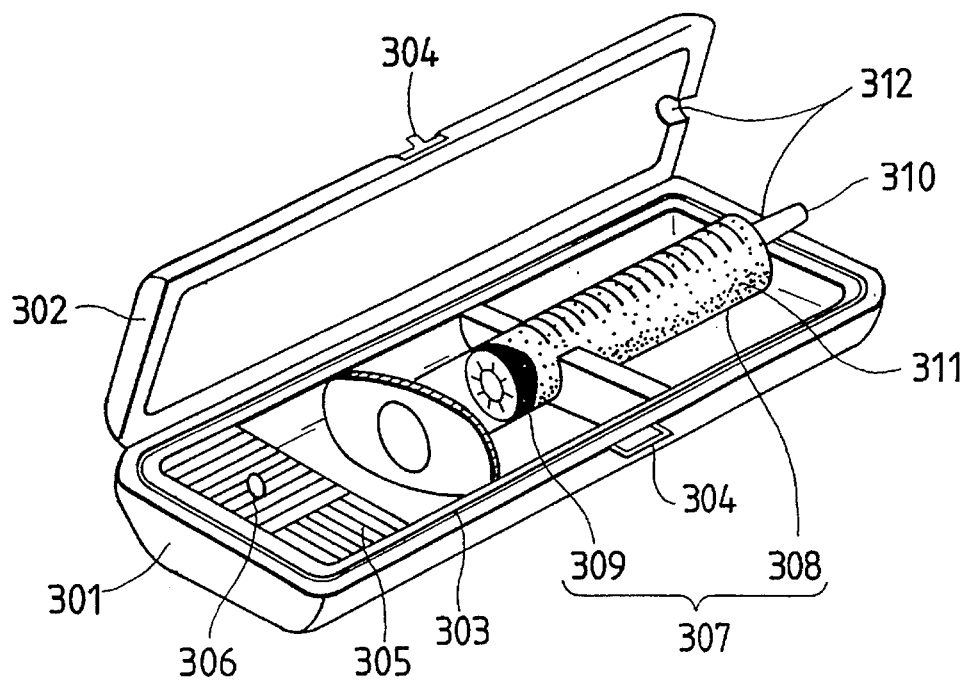
FIG. 3 is a schematic illustration of the electrochemical fluid delivery device of the present invention to be explained in Example 2, wherein the electrochemical fluid delivery device uses a fluid reservoir part in which the outer tube of a syringe and the piston are combined.

A schematic illustration of the electrochemical fluid delivery device is shown in FIG. 3. In FIG. 3, numeral 301 designates a case, numeral 302 designates a cover, numeral 303 designates an O-ring, and numeral 304 designates a metal fitting. The cover 302 is capable of being opened and closed. The cover 302 is closed and fastened by the metal fitting 304 so that the inside of the case can be maintained in an air tight condition. A power supply part 305 and electrochemical cell part 306 are provided in the case 301. Numeral 307 designates a disposable type syringe available in the market with a volume content of 5 ml. In this case, the disposable type plastic syringe is used for the fluid reservoir part. The syringe includes the outer tube 308 and the piston 309 which is previously removed from the suction member of the syringe. The piston 309 can be moved in the outer tube 308 being closely contacted with the inside of the outer tube 308. Numeral 310 designates a fluid delivery port, numeral 311 designates a liquid medicine to be delivered, and numeral 312 designates a hole through which the fluid delivery port 310 is protruded from the case 301.

In case of using this electrochemical fluid delivery device, the outer tube 308 of the syringe is filled with the liquid medicine 311 by the method shown in FIG. 2, and then the outer tube 308 of the syringe is arranged in the case 301. Next, the cover 302 is closed with respect to the case 301 and fastened by the metal fitting 304 so that the outer tube 308 of the syringe is accommodated in the case 301 in an airtight condition, and the fluid delivery port 310 is protruded from the case 301. In this example, the same electrochemical cell part as that of Example 1 is used, and a constant current is made to flow in the same manner as Example 1. Consequently, oxygen generated by the electrolysis of water accumulates in the closed case 301 to increase the pressure in the case 301 so that the piston 309 is pushed into the outer tube 308, whereby the liquid medicine 311 is delivered from the fluid delivery port 310 in the same manner as that of Example 1.

EXAMPLE 3

The other example of the electrochemical fluid delivery device of the present invention will be explained as follows, in which the fluid reservoir part is directly pushed by the gas generated in the electrochemical cell part.

Figure 4:
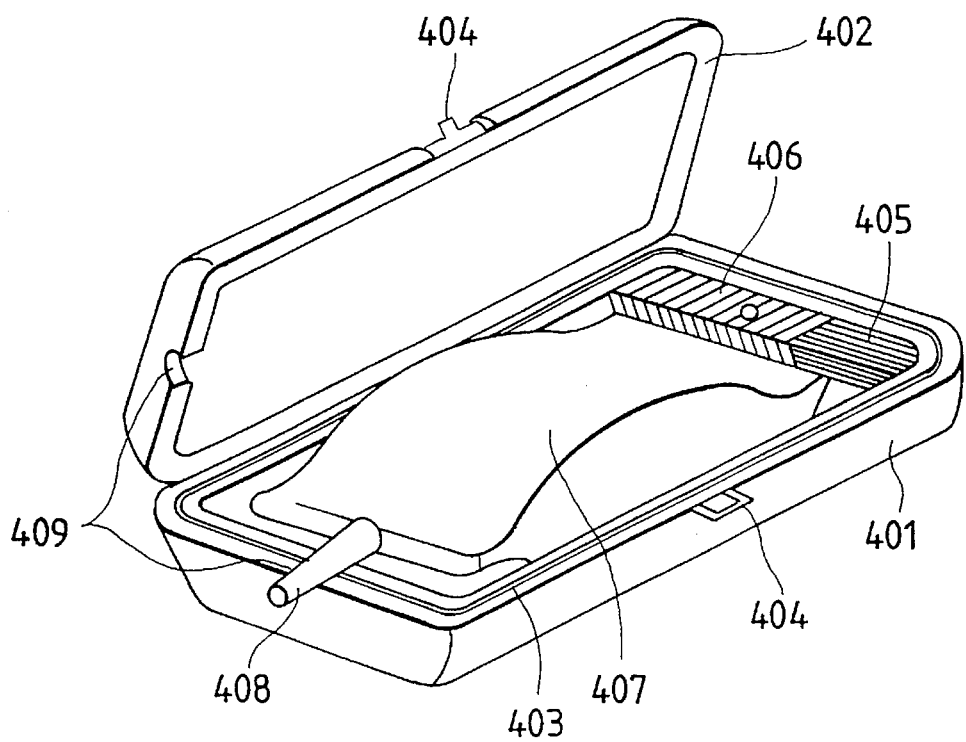
FIG. 4 is a schematic illustration of the electrochemical fluid delivery device of the present invention to be explained in Example 3, wherein the electrochemical fluid delivery device uses a fluid reservoir part comprised of a deformable bladder.

A schematic illustration of the electrochemical fluid delivery device is shown in FIG. 4. In FIG. 4, numeral 401 designates a case, numeral 402 designates a cover, numeral 403 designates an O-ring, and numeral 404 designates a metal fitting. The cover 402 is capable of being opened and closed with respect to the case 401. When the cover 402 is closed, the inside of the case can be maintained in an air tight condition. A power supply part 405 and electrochemical cell part 406 are provided in the case 401. Numeral 407 designates a bladder made of soft rubber which is used for the fluid reservoir part. A fluid delivery port 408 is attached to this bladder 407. Numeral 409 designates a hole through which the fluid delivery port 408 is protruded from the case 401.

In order to use this electrochemical fluid delivery device, first, the bladder 407 made of rubber filled with liquid medicine is arranged in the case 401. Second, the case 401 and the cover 402 are fastened by the metal fitting 404 so that the inside of the case 401 can be maintained in an airtight condition. In this connection, the fluid delivery port 408 is maintained to be out of the closed case 401. The same electrochemical cell part as that of Example 1 is used in this example. In the case where oxygen generated by the anode accumulates in the closed case 401 after feeding a constant current of 40 mA from the power supply part 405 to the electrochemical cell part 406, the pressure in the airtight case 401 increases so as to push the bladder 407 made of rubber, whereby the liquid medicine is delivered from the fluid delivery port 409 at a rate of 6 ml per hour.

EXAMPLE 4

Essentially the same electrochemical fluid delivery device as that of Example 3 was made. In this example, a check valve was attached to the inside of the fluid delivery port. The characteristics of this fluid delivery device were the same as those of Example 3, and the liquid medicine did not leak from the fluid delivery device under the condition that the device was not used.

In the electrochemical fluid delivery device of the present invention, the gas generated in the pressure generating part pushes directly the reservoir part to deliver the fluid. Namely, a disposable type syringe or bladder is used as the fluid reservoir part, which is detachable to an airtight case capable of being opened and closed. Accordingly, the fluid reservoir part can be very easily attached to or detached from the case, and further only the fluid reservoir part can be put into disposable use and the case can be repeatedly used.

In the case where the outer tube of a syringe and the piston are used for the fluid reservoir part as described in Example 2, the suction member as shown in FIG. 2 including the tube-shaped piston rod and the piston having a small hole is used to put the liquid medicine into the outer tube. Accordingly, a predetermined amount of liquid medicine can be easily charged into the fluid reservoir.

In this connection, a disposable syringe made of plastic available in the market and a syringe made of glass may be applied to the fluid reservoir part. In order to make the fluid reservoir part more compact, the fluid reservoir part may includes only the outer tube and piston of a syringe. In this case, a fore end portion of the suction member of the syringe available in the market may be used for the first piston. Alternatively, pistons of various configurations and materials such as a cylindrical piston provided with an O-ring may be applied. When a bladder is used for the fluid reservoir part, material of the bladder is not limited to rubber used in Example 3, but a bladder made of soft plastic or a thin metal sheet, or a bellows-shaped container may be applied as long as the container can be deformed when gas pressure is applied to the container.

The pressure generating part may be provided in the case as shown in FIG. 1. Alternatively, the pressure generating part may be provided outside the case, and gas generated in the electrochemical cell part may be introduced into the case through a gas introducing pipe.

In general, all cells that generate gas in proportion to a quantity of electricity when a direct current is made to flow are available to the electrochemical cell part of the present invention. More specifically, the following cells are available to the present invention.

(1) Porous metal electrodes are joined on both sides of a solid polymer cation exchange membrane, and both the electrodes come into contact with water. Oxygen generated by the anode when a current is made to flow, or hydrogen generated by the cathode, or mixture gas of oxygen and hydrogen is utilized.

(2) A porous metal electrode to be used as an anode is joined on one side of a solid polymer cation exchange membrane, and a manganese (IV) oxide electrode to be used as a cathode is joined on the other side. Oxygen generated by the anode when a current is made to flow is utilized.

(3) A porous metal electrode to be used as an anode is joined on one side of a solid polymer anion exchange membrane, and a manganese (IV) oxide electrode to be used as a cathode is joined on the other side. Oxygen generated by the anode when a current is made to flow is utilized.

(4) An ion exchange membrane is not used for the electrolyte, and an acidic or alkaline electrolytic solution is used for electrolysis of water. Oxygen or hydrogen generated by the electrode when a current is made to flow or a mixture of both gases is utilized.

(5) An ion exchange membrane is not used for the electrolyte, but various types of inorganic proton conductors such as dodeca molybdophosphoric acid ($H_3PMo_{12}O_{40} \cdot 29H_2O$), hydrogen uranyl phosphate ($HUO_2PO_4 \cdot 4H_2O$) or hydrous antimony (V) oxide ($Sb_2O_5 \cdot 4H_2O$) are used so that water is subjected to electrolysis. Oxygen or hydrogen generated in the process of electrolysis or a mixture of gases is utilized.

Further, it is possible to greatly reduce the dimensions of the electrochemical cell part of the electrochemical fluid delivery device of present invention. Consequently, it is possible to reduce the dimensions and weight of the overall electrochemical fluid delivery device. Therefore, the electrochemical fluid delivery device of present invention can be put into portable use, and its operation is simple. Furthermore, when the electrochemical fluid delivery device of the present invention is used to deliver the liquid medicine for medical treatment use, its operation is very easy for patients.

What is claimed is:

1. An electrochemical fluid delivery device comprising:

fluid reservoir means for accumulating fluid therein;

pressure generating means for generating a pressure to deliver fluid, said pressure generating means including an electrochemical cell part in which gas is generated when a direct current is made to flow therein and power supply part for supplying the direct current to said electrochemical cell part; and a case including a cover capable of being opened and closed, said case accommodating said fluid reservoir part therein and maintaining an inside of said case in an airtight condition due to closing said cover;

wherein the fluid is delivered when said fluid reservoir means is pressurized by the action of gas generated in said electrochemical cell part.

2. An electrochemical fluid delivery device according to claim 1, wherein said fluid reservoir means is detachably provided in said case.

3. An electrochemical fluid delivery device according to claim 2, wherein said fluid reservoir means includes a fluid delivery port for delivering the fluid therefrom to an outside of said device.

4. An electrochemical fluid delivery device according to claim 3, wherein said fluid delivery port includes a check valve.

5. An electrochemical fluid delivery device according to claim 3, wherein said fluid reservoir means comprises an outer tube of a syringe and a suction member having a piston at a fore end portion thereof, said piston moving in said outer tube while said piston closely comes into contact with an inner wall of said outer tube.

6. An electrochemical fluid delivery device according to claim 3, wherein said fluid reservoir means comprises an outer tube of a syringe and a first piston which moves in said outer tube while said piston closely comes into contact with an inner wall of said outer tube.

7. An electrochemical fluid delivery device according to claim 6, wherein fluid is previously reserved in said fluid reservoir means.

8. An electrochemical fluid delivery device according to claim 6, further comprising a suction member having a second piston at a fore end thereof and a communicating hole for communicating the fore end with a rear end of said suction member, said suction member being capable of engaging in the outer tube of said syringe and inserted into the outer tube to which said first piston is provided;

wherein, before said fluid reservoir means is accommodated in said case, said a fluid delivery port is immersed in fluid to fill said fluid reservoir means with the fluid when said suction member is pulled out from said outer tube with closing said communicating hole at the rear end of said suction member.

9. An electrochemical fluid delivery device according to claim 3, wherein said fluid reservoir means comprises a bladder.

10. An electrochemical fluid delivery device according to claim 9, wherein said bladder is deformable.

11. An electrochemical fluid delivery device according to claim 10, wherein fluid is previously reserved in said bladder-shaped fluid reservoir means.

12. An electrochemical fluid delivery device according to claim 1, wherein said pressure generating means is provided in said case so that gas generated by said electrochemical cell part is introduced into said case.

13. An electrochemical fluid delivery device according to claim 1, further comprising a gas introducing pipe, wherein said pressure generating means is provided outside said case so that gas generated by said electrochemical cell part is introduced into said case through said gas introducing pipe.

14. An electrochemical fluid delivery device according to claim 1, wherein said electrochemical cell portion comprises a solid polymer cation exchange membrane and porous metal electrodes which are joined to both sides of said solid polymer cation exchange membrane, respectively, said electrodes coming into contact with water;

further wherein at least one of oxygen gas generated by an anode and hydrogen gas generated by a cathode when a current is made to flow is utilized to pressurize said fluid reservoir means to deliver the fluid.

15. An electrochemical fluid delivery device according to claim 1, wherein said electrochemical cell portion comprises a solid polymer cation exchange membrane, a porous metal electrode to be used as an anode which is joined on one side of said solid polymer cation exchange membrane and a manganese (IV) oxide to be used as a cathode which is joined the other side thereof;

further wherein oxygen gas generated by the anode when a current is made to flow is utilized to pressurize said fluid reservoir means to deliver the fluid.

16. An electrochemical fluid delivery device according to claim 1, wherein said electrochemical cell portion comprises a solid polymer anion exchange membrane, a porous metal electrode to be used as an anode which is joined on one side of said solid polymer cation exchange membrane and a manganese (IV) oxide to be used as a cathode which is joined the other side thereof;

further wherein oxygen gas generated by the anode when a current is made to flow is utilized to pressurize said fluid reservoir means to deliver the fluid.

17. An electrochemical fluid delivery device according to claim 1, wherein said electrochemical cell part comprises an anode, a cathode, and at least one of acidic and alkaline electrolytic solution which is used for electrolysis of water;

further wherein at least one of oxygen and hydrogen gas generated by said electrodes when a current is made to flow is utilized to deliver the fluid.

18. An electrochemical fluid delivery device according to claim 1, wherein said electrochemical cell part comprises an anode, a cathode and a inorganic proton conductor for electrolyzing water, said anode and said cathode being joined to both side of said inorganic proton conductor, respectively;

further wherein at least one of oxygen and hydrogen gas generated by the electrolyzation is utilized to deliver the fluid.

19. An electrochemical fluid delivery device according to claim 18, wherein said inorganic proton conductor comprises at least one of dodeca molybdophosphoric acid ($H_{3PMo12}O_{40} \cdot 29H_2O$), hydrogen uranyl phosphate ($HUO_2PO_4 \cdot 4H_2O$) and hydrous antimony (V) oxide ($Sb_2O_5 \cdot 4H_2O$).

* * * * *